United States Patent [19]

Kodama et al.

[11] 4,372,949

[45] Feb. 8, 1983

[54] TREATMENT OF CANCER WITH CARCINOSTATIC AND IMMUNOSTIMULATING AGENT CONTAINING LYSOPHOSPHOLIPID AND PHOSPHOLIPID

[75] Inventors: Yutaka Kodama; Kaoru Oyama, both of Toyama; Ryusaku Shimizu, Nanao; Masao Nakabayashi, Namekawa; Yoshifumi Nakashima, Himi; Takashi Sano; Masaaki Shibata, both of Toyama; Kiyoshi Goden, Takaoka, all of Japan

[73] Assignee: Toyama Chemical Co., Ltd., Tokyo, Japan

[21] Appl. No.: 125,800

[22] Filed: Feb. 29, 1980

[30] Foreign Application Priority Data

Mar. 5, 1979 [JP] Japan .................................. 54/24600
Sep. 14, 1979 [JP] Japan ................................. 54-117262

[51] Int. Cl.³ .................... A61K 31/685; A61K 45/05
[52] U.S. Cl. ....................................... 424/199; 424/38; 424/365
[58] Field of Search ................. 424/31, 38, 9, 14, 199, 424/365

[56] References Cited

U.S. PATENT DOCUMENTS 3,752,886 8/1973 Munder ............................... 424/199
4,119,714 10/1978 Kny ..................................... 424/199

FOREIGN PATENT DOCUMENTS 2364656 5/1977 France .
1530138 10/1978 United Kingdom .

OTHER PUBLICATIONS

Kitagawa, J. Biochem., vol. 79, 1976, pp. 1123–1133.
Sunamoto, Biochim. et Biophys. Acta, vol. 510, 1978, pp. 52–62.
Kinsky, J. Biochem. (Tokyo), vol. 79, 1976, pp. 24P–25P.
Munder, Chem. Abs., vol. 79, 1973, Ab No. 51669p.
Fauve, Chem. Abs., vol. 85, 1976, Ab No. 10434p.
Layton, Arch. Int. de Physiol. et Biochemie, vol. 87, Dec. 1979, pp. 1014–1016
Van Rooijen, Chem. Abs., vol. 88, 1978, Ab 88:20445.
Munder, Clin. Bull., vol. 6, No. 2, 1976, p. 80.

*Primary Examiner*—Anna P. Fagelson
*Attorney, Agent, or Firm*—Oblon, Fisher, Spivak, McClelland & Maier

[57] ABSTRACT

A carcinostatic and immunostimulating agent containing a lysophospholipid and a phospholipid. Said carcinostatic and immunostimulating agent is useful for the treatment of cancerous diseases of the mammals including human being. This disclosure concerns such a carcinostatic and immunostimulating agent and a process for preparing the same as well as a method for treating the cancerous diseases by using said agent.

9 Claims, No Drawings

TREATMENT OF CANCER WITH CARCINOSTATIC AND IMMUNOSTIMULATING AGENT CONTAINING LYSOPHOSPHOLIPID AND PHOSPHOLIPID

This invention relates to a carcinostatic and immunostimulating agent containing a lysophospholipid and a phospholipid and a process for preparing the same as well as a method for treating cancerous diseases by administering said agent.

Lysophospholipids have very excellent carcinostatic and immunostimulating activities. On the other hand, they also have a strong hemolysis. Therefore, these lysophopholipids per se have a great problem in safety in use as pharmaceutical products. Also, lysophospholipids are strongly bound with serum proteins to be inactivated, whereby the carcinostatic and immunostimulating activities thereof are decreased. Accordingly, there have not been known carcinostatic and immunostimulating agents comprising lysophospholipids and a substance which does not inactivate the main activity of the lysophospholipids but can reduce the hemolysis of the lysophospholipids.

Under such circumstances, the present inventors have pursued further studies and found as a result that a composition containing both lysophospholipid and phospholipid has excellent properties as a carcinostatic and immunostimulating agent and is useful as a remedial drug for cancer of the mammals, particularly human being. It has also been found that a carcinostatic and immunostimulating agent containing a fat and oil or a fat emulsion together with said composition of lysophospholipid and phospholipid, or a carcinostatic and immunostimulating agent containing a lysophospholipid and a fat emulsion, this fat emulsion corresponding to the phospholipid plus the fat and oil, also possesses said properties.

It is therefore an object of this invention to provide a carcinostatic and immunostimulating agent comprising lysophospholipids in which the hemolysis of lysophospholipids is depressed without affecting their carcinostatic and immunostimulating effect and which can be used with high safety without causing any vascular trouble even if said agent is used continuously through parenteral administration.

Another object of this invention is to provide a process for preparing such a carcinostatic and immunostimulating agent. It is a further object of this invention to provide a method for treating cancer by administering said agent.

Other objects and advantages of this invention will become apparent from the following description.

According to this invention, there is provided a carcinostatic and immunostimulating agent comprising a lysophospholipid and a phospholipid, and optionally a fat emulsion and a fat and oil.

In the carcinostatic and immunostimulating agent comprising a lysophospholipid of this invention, it is preferred that the lysophospholipid is dispersed in the form of micells or lipid vesicles, and it is particularly preferable that the dispersed particles have a particle size of not more than $1.0\mu$, more preferably not more than $0.5\mu$. As far as the lysophospholipid is dispersed in the form of micells or lipid vesicles, the addition of serum proteins (albumin) to said dispersion does not affect at all the carcinostatic and immunostimulating activities of the lysophospholipids.

The phospholipid used in this invention may be one derived from natural products such as yolk, soybean, cottonseed, rapeseed, corn, peanut, etc., or may be a purely synthesized phospholipid. Also, in the case of a phospholipid having an unsaturated fatty acid residue, it may be converted into a type having a saturated fatty acid residue by a suitable operation such as hydrogenation. As examples of the phospholipid, there may be mentioned lecithin, phosphatidyl ethanolamine, phosphatidyl serine, sphingomyelin, phosphatidyl inositol, phosphatidic acid and the like, and these substances may be used either singly or in admixture. Preferred is lecithin derived from a natural product, particularly yolk.

The lysophospholipids usable in this invention include, for example, glycerophospholipids (phosphoglycerides) from which only one fatty acid has been removed, such as, for example, lysolecithin, lysocephalin, lysoplasmalogen, lysophosphatidic acid, lysophosphatidyl inositol and the like as well as compounds represented by the following formula:

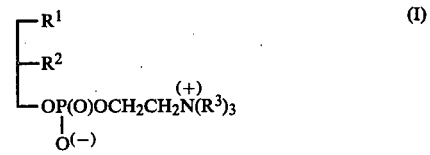

wherein $R^1$ is a $C_{5\text{-}22}$ acyloxy or $C_{5\text{-}22}$ alkoxy group, $R^2$ is a hydrogen atom or a hydroxyl, $C_{1\text{-}5}$ acyloxy or $C_{1\text{-}5}$ alkoxy group, and $R^3$ is a hydrogen atom or a $C_{1\text{-}5}$ alkyl group, said $R^1$ and $R^2$ being interchangeable with each other. These lysophospholipids may be ones derived from natural products, for example, swine cerebrum, or may be ones derived from said phospholipid enzymatically or by a chemical synthesis. As examples of the $C_{5\text{-}22}$ acyloxy groups represented by $R^1$ in formula (I), there may be mentioned $C_{5\text{-}22}$ alkanoyloxy or $C_{5\text{-}22}$ alkenoyloxy groups. Preferred examples of said lysophospholipids for use in this invention are lysolecithin having a $C_{14\text{-}18}$ alkanoyloxy or $C_{14\text{-}18}$ alkenoyloxy group and ether type lysolecithin (a compound of formula (I) in which $R^1$ is an octadecyloxy group, $R^2$ is a methoxy group and $R^3$ is a methyl group).

The phospholipids and lysophospholipids used in this invention exist usually in the D-, L- or DL-forms, and any of these forms may be used though the L-form is particularly preferred.

The mixing ratio of phospholipid to lysophospholipid in the carcinostatic and immunostimulating agent according to this invention may preferably be in the range of 1.0–500 to 1, preferably 5–20 to 1 by weight.

The carcinostatic and immunostimulating agent of the above-mentioned composition may further contain a fat and oil. Any known type of fats and oils may be used in this invention provided that they are pharmaceutically acceptable ones, but it is desirable to use an edible oil such as cottonseed oil, soybean oil, corn oil, coconut oil, rapeseed oil, sesame oil or peanut oil. In this case, the mixing ratio of the lysophospholipid, the phospholipid and the fat and oil is preferably such that per 1 part by weight of the lysophospholipid, the amounts of the phospholipid and the fat and oil are 1.0 to 500 parts by weight and not more than 200 parts by weight, respectively, and more preferably such that they are 5 to 20 parts by weight and not more than 20 parts by weight, respectively.

The fat emulsions usable in the carcinostatic and immunostimulating agent of this invention include those composed of 0.1 to 50 parts by weight of an emulsifier such as said phospholipid and 5.0 to 200 parts by weight of water per 10 parts by weight of a fat and oil. As preferred examples of such fat emulsions, there may be mentioned Intrafat or Intralipid (both being registered trademarks) consisting of 10 parts by weight of soybean oil, 1.2 parts by weight of yolk phospholipid, 86.3 parts by weight of water and 2.5 parts by weight of concentrated glycerin, which is an isotonic agent, Fatgen (registered trademark), Lipofundin-S (trademark of Braun Melsungen, Germany), Lipihysan (trademark of Egic, France) and the like. In this case, the mixing ratio of the lysophospholipid to the fat emulsion may be such that the lysophospholipid is contained in an amount of 0.1 to 50 mg per 1 ml of the fat emulsion, and it is preferable that the composition contains the lysophospholipid in an amount of 1 to 10 mg per 1 ml of the fat emulsion which contains 5-30% by weight of lipid.

When the carcinostatic and immunostimulating agent of this invention comprises the lysophospholipid, the phospholipid and the above-mentioned fat emulsion, the amount of the fat emulsion may be such as not to exceed 5,000 ml per 1 mg of the lysophospholipid of the mixture of lysophospholipid and phospholipid.

The carcinostatic and immunostimulating agent of this invention may also contain, in addition to said constituents, other additives which are commonly used in the medicinal preparations, such as isotonic agents, for example, glycerin, sorbitol, xylitol, sodium chloride, dextrose or the like; antioxidants such as vitamin A, vitamin E or the like; cholesterol; stearylamine; dicetyl phosphate; dextran; methionine; glutathione; or the like according to the purpose of use. It may also contain an isotonic solution such as water, a 5% dextrose solution, physiological salt solution or the like. The use and mixing of the constituents may be conducted in any conventional manner.

The pharmacological effects of the carcinostatic and immunostimulating agent of this invention is described below.

(A) Hemolysis

The hemolysis was determined in the following way: A suspension of rabbit erythrocytes and the compound to be tested were mixed and shaken at 37° C. for one hour, and the optical density (hereinafter referred to as O.D.) at 550 mμ of the supernatant of the centrifuged solution was measured. The optical density at the time of perfect hemolyzation with distilled water was given as 100%, and the density of the test compound at 50% hemolyzation was represented as an index for indicating the degree of hemolysis. When O.D. was unmeasurable, the hemolysis was judged by the naked eye and expressed by signs (+) and (−). The results are shown in Tables 1 and 2.

TABLE 1

| Test compd. No. | Series of dilutions of L-lysolecithin (μg/ml) | | | | | | | | | | | | |
|---|---|---|---|---|---|---|---|---|---|---|---|---|---|
| | 4000 | 2000 | 1000 | 500 | 250 | 125 | 62.5 | 31.3 | 15.7 | 7.8 | 3.9 | 2.0 | 1.0 |
| L-lysolecithin | +++ | +++ | +++ | +++ | +++ | +++ | +++ | +++ | ++ | + | ± | − | − |
| 1*1 | − | − | − | − | − | − | − | − | − | − | − | − | − |
| 2*2 | − | − | − | − | − | − | − | − | − | − | − | − | − |
| 3*3 | − | − | − | − | − | − | − | − | − | − | − | − | − |
| 4*4 | ++ | ++ | ++ | + | − | − | − | − | − | − | − | − | − |

Note:
O.D. at 550 mμ: +++ = 100–80%, ++ = 80–60%, + = 60–30%, ± = 30–10%, − = <10%.
*1 The solution obtained in Preparation Example 8 shown hereinafter was used as base solution.
*2 The solution obtained in Preparation Example 6 shown hereinafter was used as base solution.
*3 The solution obtained in Preparation Example 2 shown hereinafter was used as base solution.
*4 The fat emulsion (comprising 2.5 parts by weight of concentrated glycerin, 1.2 parts by weight of yolk phospholipid and 86.3 parts by weight of water per 10 parts by weight of soybean oil) is contained in a concentration of 0.25 ml in the final solution.

TABLE 2

Relationship between hemolysis and concentrations of fat emulsion and L-lysolecithin

| Fat emulsion* concentration (%) | L-lysolecithin concentration (mg/ml) | | | | | | | | | |
|---|---|---|---|---|---|---|---|---|---|---|
| | 20 | 10 | 5 | 2.5 | 1.25 | 0.62 | 0.31 | 0.16 | 0.08 | 0.04 |
| 90 | + | + | + | ± | − | − | − | − | − | − |
| 75 | + | + | + | ± | − | − | − | − | − | − |
| 50 | + | + | + | ± | ± | − | − | − | − | − |
| 25 | + | + | + | + | + | ± | ± | − | − | − |
| 12.5 | + | + | + | + | + | + | ± | ± | − | − |
| 6.2 | + | + | + | + | + | + | ± | − | − | − |
| 3.1 | + | + | + | + | + | + | + | ± | − | − |
| 0 | + | + | + | + | + | + | + | + | + | + |

Note:
+: hemolyzed,
±: partially hemolyzed,
−: unhemolyzed
*The fat emulsion comprises 2.5 parts by weight of concentrated glycerin, 1.2 parts by weight of yolk phospholipid and 86.3 parts by weight of water per 10 parts by weight of soybean oil.

(B) Minimum inhibitory concentration of cancerous cells (MIC)

The antitumor effect of each test compound was determined under the following conditions by using the Hela S-3 strain and Ehrlich's ascites tumor cells each in a population of $2 \times 10^4$ cells/ml.

| (1) Culture medium: | Eagle's MEM + 20% bovine embryonic serum |
|---|---|
| (2) Culture time: | 96 hrs. |
| (3) Microplate assay: | Diluted down in 12 stages from 5,000 μg/ml |
| (4) Method of judgement: | The test compound concentration at which the growth of cells was inhibited more than 50% in Giemsa's staining was represented as MIC. |

The results are shown in Table 3.

TABLE 3

| | Type of cancerous cells MIC (μg/ml) | |
|---|---|---|
| Test compd. No. | Hela | Ehrlich |
| 1 | 156 | 156 |
| 5* | 156 | 313 |
| 6** | 78 | 313 |

TABLE 3-continued

| Test compd. No. | Type of cancerous cells MIC (μg/ml) | |
|---|---|---|
| | Hela | Ehrlich |
| L-lysolecithin | 156 | 156 |

Note:
*A dilution of the solution obtained in Preparation Example 5 shown hereinafter.
**A dilution of the solution obtained in Preparation Example 1 shown hereinafter.

(C) Pre-administration effect to L-1210 (L-1210 allograft)

Each test compound was repeatedly administered (at a dose of 40 mg/kg as calculated in terms of L-lysolecithin) intraperitoneally to ddN strain mice (male, 6-week old) for a period of 7 days, and after one-week no-administration period, $1 \times 10^6$ L-1210 leukemic cells were inoculated intraperitoneally and the average number of survival days of the test animal was determined. The results are shown in Tables 4 and 5.

TABLE 4

| Test compound. No. | n (animals) | Average number of survival days |
|---|---|---|
| Control | 6 | 9.0 |
| L-lysolecithin | 6 | >21.0 |
| 1 | 6 | >21.0 |

(Each test compound was given so that the amount of L-lysolecithin was 40 mg/kg.)

TABLE 5

| Test compd. No. | Number of survival days (mean ± S.E.) | Number of survivor for 21 days/Number of mice tested |
|---|---|---|
| Control | 12.0 ± 3.4 | 0/6 |
| L-lysolecithin* | 21.0 | 6/6 |
| 7** | 18.5 ± 2.5 | 5/6 |

Note:
*Given at a dose of 40 mg/kg.
**40 mg/kg of L-lysolecithin + 20 ml/kg of fat emulsion
Fat emulsion composition:
| Soybean oil | 10 |
| Glycerin | 2.5 |
| Yolk phospholipid | 1.2 |
| Water | 86.3 |

(D) Inhibitory effect against metastasis of Lewis lung cancer $1 \times 10^6$ Lewis lung cancerous cells were given intravenously to BDF$_1$ strain (female, 13-week old) mice, and after 24 hours, L-lysolecithin (40 mg/kg) was administered intraperitoneally while a mixture of a fat emulsion (20 ml/kg) and L-lysolecithin (40 mg/kg) was administered intravenously, each for a period of 10 days repeatedly, and at the 11th day, the breast of each test mouse was cut open and the dry weight of the lung (mg mean ± S.E.) was measured. The inhibitory effect was judged by the ratio to the control group (T/C). The results obtained are shown in Table 6.

TABLE 6

| Test compd. No. | n (animals) | Dry lung weight (mg mean ± S.E.) | Increased weight (mg mean ± S.E.) | T/C (%) |
|---|---|---|---|---|
| Untreated group | 6 | 29.6 ± 0.4 | — | — |
| Control | 8 | 44.9 ± 5.6 | 16.3 ± 5.6 | 100 |
| L-lysolecithin | 6 | 34.3 ± 1.6 | 4.7 ± 1.6 | 29.0 |
| 7 | 6 | 34.3 ± 1.7 | 5.0 ± 1.7 | 30.7 |

(E) Remedial effect for Ehrlich's ascites tumor

Ehrlich's ascites tumor cells were inoculated intraperitoneally to ddN-strain mice (female, 6-week old), and after 24 hours from said inoculation, each test compound was repeatedly administered intraperitoneally (i.p.) for a period of 7 days or intravenously (i.v.) for a period of 13 days, and the life-prolonging and tumor-remedial effects were examined. The results obtained are shown in Table 7.

TABLE 7

| Test compd. No. | Dose (ml/day) | Administration route | Number of cancerous cells inoculated (cells/ml) | n (animals) | Number of survival days (mean ± S.E.) | T/C (%) |
|---|---|---|---|---|---|---|
| Control | — | — | $1 \times 10^5$ | 6 | 20.6 ± 0.7 | — |
| 1 | 0.4 | i.p. | $1 \times 10^5$ | 6 | >45 | >217 |
| 1 | 0.8 | " | $1 \times 10^5$ | 6 | >45 | >217 |
| 2 | 0.2 | i.v. | $1 \times 10^5$ | 6 | 30.7 ± 2.6 | 175 |

(F) Effect against P-388 leukemic cells 0.5 ml of a dispersion of Test Compound No. 1 and $5 \times 10^6$ P-388 leukemic cells were mixed and shaken at 37° C. for one hour, after which no destruction of the P-388 leukemic cells was confirmed (by Trypan Blue staining). 0.2 ml of the shaken solution was then inoculated intraperitoneally to BDF$_1$ strain mice (female, 12-week old) and the life-prolonging effect of the compound was examined. The results obtained are shown in Table 8.

TABLE 8

| Test compd. No. | Survival days (mean ± S.E.) | Number of survivor for 40 days/Number of tested mice | T/C (%) |
|---|---|---|---|
| Control | 12.4 ± 0.2 | 0/8 | — |
| 2 (0.5 ml) | >40 | 8/8 | >322 |

(G) Acute toxicity

The results of measurement of acute toxicity on some typical compounds prepared according to this invention are shown in Table 9.

TABLE 9

| Test compound No. | LD$_{50}$ (mg/kg) |
|---|---|
| L-lysolecithin | 122 |
| 8* | 188*** |
| 9** | >600*** |

(Test animal: mice, female; intravenous injection)
Note:
*compound prepared in Preparation Example 9
**compound prepared in Preparation Example 5
***amount of L-lysolecithin in the composition It will be understood from Tables 1 to 9 that the carcinostatic and immunostimulating agent according to this invention is markedly reduced in its hemolysis while maintaining the peculiar carcinostatic and immunostimulating effect of the lysophospholipids and is also high in safety in use.

The process for the preparation of the carcinostatic and immunostimulating agent according to this invention is described below.

Although the compositions of this invention may be prepared according to a usual process, it is preferred to employ a method which is usually used for obtaining a composition consisting of fine particles.

Generally, ultracentrifugation, dialysis, gel column chromatography or other like means is used for obtaining a mixture composed of particles with small sizes, but these techniques are very complicated in actual operation and undesirable as means for mass production of a commercial product.

Therefore, the present inventors have made further research on an industrially advantageous method and found as a result that the membrane filter method in which the dispersion obtained by mixing the respective component materials is filtered by a membrane filter has such characteristics that it enables one to obtain only particles with small particle sizes, is very simple in operation and also allows a simultaneous aseptic treatment, and that the composition obtained according to said method meets the object of this invention.

Said method is more specifically described.

A carcinostatic and immunostimulating agent comprising a lysophospholipid and a phospholipid can be obtained by first dissolving the lysophoshilipid and the phospholipid uniformly in a halogenated hydrocarbon such as chloroform, methylene chloride, or the like, or an alcohol such as methanol, ethanol, etc., or a mixed solvent thereof, under a nitrogen atmosphere, then distilling off the solvent and adding to the residue water (if necessary, an isotonic solution such as a 5% dextrose solution or a physiological salt solution may be used instead of the water), followed by sufficient mixing, or alternatively by first dissolving the phospholipid uniformly in said organic solvent, then distilling off the solvent and adding to the residue a solution prepared by dissolving a lysophpholipid uniformly in water (if necessary an isotonic solution such as a 5% dextrose solution or a physiological salt solution may be used instead of the water), followed by sufficient mixing, or alternatively, by adding the lysophospholipid and the phospholipid directly to water (if necessary, an isotonic solution such as a 5% dextrose solution or a physiological salt production may be used instead of the water), homogenizing the mixture, and then throughly mixing the same. The thus obtained dispersion is then subjected to a mechanical dispersing treatment such as supersonic treatment or ejection under pressure for reducing the size of the particles and then filtered through a membrane filter, whereby a favorable dispersion is obtained. This dispersion may be immediately put to use, or if necessary, it may be freeze-dried in a vacuum in the usual way to form a solid product.

In carrying out the above-mentioned operation, the following instructions are to be noted. The amount of the organic solvent used, which is not subjected to any specific limitation, may be more than the amount capable of perfectly dissolving the solute. The solvent used is distilled off at a temperature as low as possible, preferably not more than 40° C. Then, to the solution is added water or an isotonic solution, which may contain a lysophospholipid, and mixed at room temperature for a period of 30 minutes to 3 hours. In this case, in order to enhance the mixing efficiency, it is recommended to add a suitable quantity of glass beads and rotate the container itself, or directly adding the lysophospholipid and phospholidpid to water (if necessary, an isotonic solution such as a 5% dextrose solution or a pharmacological salt solution may be used instead of the water) and then mixing the mixture by a high speed mixer and a mechanical didpersing treatment as mentioned above.

The mixed solution (after removing the glass beads where they were used) is then subjected to a mechanical dispersing treatment, for example a supersonic treatment under the conditions of 9–200 KHz and 50–1,500 W for a period of 10 minutes to 10 hours and then filtered at atmospheric pressure, under pressure (3 kg/cm$^2$ or less) or under reduced pressure by using a membrane filter (for example, cellulose acetate or tetrafluoroethylene polymer, etc.) with a mesh size of not more than 1$\mu$, preferably not more than 0.5$\mu$. When the filtrate is subjected to freeze-drying, it is preferably performed in vacuo by maintaining the temperature below 30° C. at the final stage.

When it is desired to obtain a composition which contains a fat and oil in addition to the said components, the fat and oil are added to the dispersion obtained by the above-mentioned method or a dispersion obtained by dissolving a lysophospholipid and a phospholipid uniformly in a halogenated hydrocarbon such as chloroform or methylene chloride or an alcohol such as methanol or ethanol, or a mixed solvent thereof under a nitrogen atmosphere, removing the solvent by distillation, adding to the residue thus obtained water (if necessary an isotonic solution such as a 5% dextrose solution or a physiological salt solution may be used instead of the water), and then thoroughly mixing the same. The resulting mixture is thoroughly mixed and then subjected to a supersonic treatment and filtration through a membrane filter in the manner described above to obtain a dispersion. Alternatively, the lysophospholipid, the phospholipid and the desired fat and oil are dissolved uniformly in an organic solvent such as those mentioned above, the solvent is removed by distillation, and to the residue was added water (if necessary an isotonic solution such as a 5% dextrose solution or a physiological salt solution may be used instead of the water), and this mixture, after sufficient mixing, is subjected to a mechanical dispersing treatment and filtration through a membrane filter in the manner discribed above to obtain a desired dispersion.

For obtaining a composition containing a lysophospholipid, a phospholipid and a fat emulsion, the fat emulsion is added to a dispersion containing the lysophospholipid and the phospholipid, the dispersion being obtained in the manner said above, and the resulting mixture is shaken several times. In this case, since the dispersed particles are small in size, said dispersing treatment and filtration through a membrane filter may be performed as occasion demands.

For obtaining a carcinostatic and immunostimulating agent containing a lysophospholipid and a fat emulsion, the lysophospholipid is dissolved in water (if necessary an isotonic solution such as a 5% dextrose solution or a physiological salt solution may be used instead of the water), and to this solution is added the fat emulsion, after which the resulting mixture is shaken several times. In this case, as the particles are generally small in size, said dispersing treatment and filtration through a membrane filter may be performed when needed. The conditions for these operations are same as those used in the afore-said production methods.

The carcinostatic and immunostimulating agent according to this invention can be formulated into any usual form of medicine by using a commonly known additive or additives such as mentioned above according to the purpose of use or the form of medicinal preparation.

Also, the carcinostatic and immunostimulating agent of this invention is appliable for the treatment of various types of cancer, for example, cancer of internal organs such as lung, liver, pancreas, digestive organs, etc., as well as other diseases such as leukemia and sarcoma, for example, osteosarcoma. The method of administration, the number of repetitions of administration and the dosage may be varied appropriately according to the patient's conditions but usually the drug containing 0.1–200 mg/kg of a lysophospholipid is administered either orally or parenterally one to four times a day for the adult. As for the method of administration, intravenous or intramuscular injection, particularly intravenous drip injection is preferred.

The invention is described in further detail hereinbelow by reference to some typical examples of medicinal preparations.

PREPARATION EXAMPLE 1

9.6 g of yolk lecithin, 1.0 g of L-lysolecithin and 1.0 g of vitamin E were dissolved in 40 ml of chloroform, and the chloroform was removed by distillation under reduced pressure at a temperature of not more than 40° C., after which the residue was further dried in vacuo at room temperature for 2 hours. To the resultant product was added 100 g of glass beads and 100 ml of a 5% dextrose solution for injection, and the container was rotated for a period of 1.5 hours to obtain a dispersion. The glass beads were removed by filtration and the filtrate was subjected to a supersonic treatment (28 KHz; 150 W) for a period of 2.5 hours and then filtered under pressure by using a membrane filter with a mesh size of $0.3\mu$. The resultant filtrate was further subjected to a sterilization treatment and divided into 25-ml vials for intravenous injection, and the vials were sealed to obtain injections (turbidity 6% as measured using a sphere method turbidity meter of type SEP-PL in which the test sample was placed in a 10-mm length path cuvette and a bulb of 12 V and 15 W was used).

PREPARATION EXAMPLE 2

50 ml of the dispersion for intravenous injection obtained in Preparation Example 1 and 50 ml of a separately prepared fat emulsion (200 ml of an aqueous emulsion containing 20 g of soybean oil, 5.0 g of concentrated glycerin and 2.4 g of yolk phospholipid) were mixed and the mixture was subjected to a supersonic treatment and filtration through a membrane filter in the same manner as in Preparation Example 1 to obtain an intravenous drip injection.

PREPARATION EXAMPLE 3

20 ml of the dispersion for intravenous injection obtained in Preparation Example 1 was added to 200 ml of a commercially available fat emulsion (Intrafat) and the mixture was shaken two to three times to obtain an intravenous drip injection.

PREPARATION EXAMPLE 4

10 ml of the dispersion for intravenous injection obtained in Preparation Example 1 was freeze-dried in vacuo to obtain an intravenous drip injection which could be adjusted to the necessary concentration when used.

PREPARATION EXAMPLE 5

1 g of L-lysolecithin, 9.6 g of yolk lecithin and 1 g of sesame oil were dissolved in 40 ml of chloroform and the chloroform was removed by distillation under reduced pressure at a temperature of not more than 40° C., after which the residue was further dried in vacuo at room temperature for 2 hours. The resultant product was mixed with 100 g of glass beads and 100 ml of a 5% dextrose solution for injection, and the container was rotated for a period of 1.5 hours to obtain a dispersion. The glass beads were removed by filtration and the filtrate was subjected to a supersonic treatment (28 KHz; 150 W) for 2.5 hours and then filtered under pressure by using a membrane filter with a mesh size of $0.3\mu$, and the resultant filtrate was further subjected to a sterilization treatment and divided into 2-ml vials for intravenous injection, and the vials were sealed to obtain injections (tunbidity 20%).

PREPARATION EXAMPLE 6

9.6 g of yolk lecithin and 1.6 g of L-lysolecithin were dissolved in 40 ml of chloroform, and the chloroform was removed by distillation under reduced pressure at a temperature of not more than 40° C., after which the residue was dried in vacuo at room temperature for 2 hours. To this product were then added 100 g of glass beads and 100 ml of a 5% dextrose solution for injection, and the container was rotated for 1.5 hours to obtain a dispersion. The glass beads were removed by filtration and the filtrate was subjected to a supersonic treatment (28 KHz; 150 W) for a period of 2.5 hours and then filtered through a membrane filter with a mesh size of $0.3\mu$, and the obtained filtrate was further subjected to a sterilization treatment and divided into 2-ml vials for intravenous injection, and the vials were sealed to obtain injections.

PREPARATION EXAMPLE 7

20 ml of the dispersion for intravenous injection prepared in Preparation Example 1 was added to 200 ml of a commercial fat emulsion (Intrafat) and the mixture was shaken 2 to 3 times to obtain an intravenous drip injection.

PREPARATION EXAMPLE 8

9.6 g of yolk lecithin and 1 g of L-lysolecithin were dissolved in 40 ml of chloroform, and the chloroform was removed by distillation under reduced pressure at a temperature of not more than 40° C., after which the residue was dried in vacuo at room temperature for a period of 2 hours. To the resultant product were added 100 g of glass beads and 100 ml of a 5% dextrose solution for injection and the container was rotated for a period of 1.5 hours to obtain a dispersion. Then the glass beads were removed by filtration and the filtrate was subjected to a supersonic treatment (28 KHz; 150 W) for a period of 2.5 hours and then filtered through a membrane filter with a mesh size of $0.3\mu$, and the resultant filtrate was further subjected to a sterilization treatment, divided into 2-ml vials for intravenous injection and the vials were sealed to obtain injections.

PREPARATION EXAMPLE 9

1.0 g of sterilized L-lysolecithin was dissolved in 100 ml of a physiological salt solution for injection and the solution was subjected to aseptic filtration and sealed into 2-ml ampoules for injection to obtain injections.

Said injection ampoule solution was added, in an amount of up to 10 ampoules according to the purpose of use, to a separately prepared fat emulsion (200 ml of an aqueous solution containing 20 g of soybean oil, 5.0 g of concentrated glycerin and 2.4 g of yolk phospholipid) and the mixed solution was shaken 2 to 3 times to obtain an intravenous drip injection.

PREPARATION EXAMPLE 10

An ampoule solution for drip (already subjected to aseptic filtration) consisting of 200 mg of L-lysolecithin dissolved in 20 ml of a physiological salt solution was added to 500 ml of a commercially available fat emulsion (Intrafat), and the mixed solution was shaken 2 to 3 times to obtain an intravenous drip injection.

PREPARATION EXAMPLE 11

15 g of soybean lecithin, 1.0 g of L-lysolecithin and 1.0 g of vitamin E were dissolved in 40 ml of chloroform, and the chloroform was removed by distillation under reduced pressure at a temperature of not more than 40° C., after which the residue was further dried in vacuo at room temperature for a period of 2 hours. To the resultant product were added 100 g of glass beads and 100 ml of a 5% dextrose solution for injection and the container was rotated for a period of 1.5 hours to obtain a dispersion. The glass beads were removed by filtration and the filtrate was subjected to a supersonic treatment (19 KHz; 1,200 W) for a period of 2.5 hours and filtered under pressure through a membrane filter with a mesh size of $0.5\mu$, and the obtained filtrate was further subjected to a sterilization treatment, divided into 25-ml vials for intravenous injection, and the vials were sealed to obtain injections.

PREPARATION EXAMPLE 12

9.6 g of yolk lecithin and 1.0 g of 1-octadecyl-2-methyl-3-phosphorylcholine were dissolved in 40 ml of chloroform, and the chloroform was removed by distillation under reduced pressure at a temperature of not more than 40° C., after which the residue was further dried in vacuo at room temperature for 2 hours. After adding thereto 100 g of glass beads and 100 ml of a physiological salt solution, the container was rotated for a period of 2 hours to obtain a dispersion. Then the glass beads were removed by filtration and the filtrate was subjected to a supersonic treatment (28 KHz; 150 W) for a period of 2.5 hours and filtered under pressure through a membrane filter with a mesh size of $1\mu$, and the resultant filtrate was further subjected to a sterilization treatment, and divided into 25-ml vials for intravenous injection, after which the vials were sealed to obtain injections.

PREPARATION EXAMPLE 13

50 ml of the dispersion for intravenous injection prepared in Preparation Example 1 and 50 ml of a separately prepared fat emulsion (200 ml of an aqueous emulsion containing 20 g of sesame oil, 5.0 g of concentrated glycerin and 2.4 g of yolk phospholipid) were mixed and the mixture was subjected to a supersonic treatment under the same conditions as in Preparation Example 1 and then filtered through a membrane filter with a mesh size of $0.2\mu$ to obtain an intravenous drip injection.

PREPARATION EXAMPLE 14

9.6 g of yolk lecithion and 1.0 g of L-lysolecithin were added to 90 ml of a 5% dextrose solution for injection, and the mixture was homogenized by a high speed mixer for a period of 30 minutes. The resulting dispersion was subjected to a supersonic treatment (19 KHz, 1200 W) for a period of one hour, and then filtered under pressure (0.5-1 kg/cm$^2$) by use of a membrane filter of cellulose acetate with a mesh size of $0.2\mu$. The resultant filtrate was further subjected to a sterilization treatment and divided into 25-ml vials for intravenous injection.

What is claimed is:

1. A method for treating a host mammal having cancer, which comprises administering to said host mammal a therapeutically effective amount of a composition comprising a lysophospholipid and a phospholipid in an amount of 1 part by weight of lysopholidpid to from 1.0-500 parts by weight of phospholipid.

2. The method according to claim 1, wherein the composition is in the form of lipid vesicles.

3. The method according to claim 2, wherein the lipid vesicles have a particle size of not more than $1.0\mu$.

4. The method according to claims 1, 2 or 3 wherein the lysophospholipid is a compound of the formula:

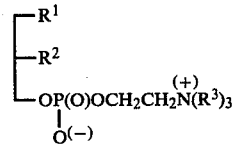

wherein $R^1$ is a $C_5$-$C_{22}$ acyloxy or $C_5$-$C_{22}$ alkoxy group, $R^2$ is hydrogen, hydroxyl, $C_{1-5}$ acyloxy, or $C_{1-5}$ alkoxy group, and $R^3$ is hydrogen or $C_{1-5}$ alkyl group, said $R^1$ and $R^2$ being interchangeable with each other.

5. The method according to claims 1, 2 or 3 wherein the lysophospholipid is lysolecithin.

6. The method according to claims 2 or 3 wherein the lysophospholipid is lysolecithin and the phospholipid is lecithin.

7. The method of claim 1 wherein there is 1 part by weight of lysophospholipid to from 5-20 parts by weight of phospholipid.

8. A method for treating a mammal having cancer, which comprises administering to said mammal a composition comprising a lysophospholipid and a phospholipid wherein the phospholipid is in the form of a fat emulsion, and there is from 0.1 to 50 mg lysophospholipid per 1 ml of fat emulsion.

9. The method of claim 8 wherein the lysophospholipid is in amount of from 1 to 10 mg per 1 ml of the fat emulsion.

* * * * *